United States Patent
Liu et al.

(10) Patent No.: US 7,587,950 B2
(45) Date of Patent: Sep. 15, 2009

(54) SOURCE DILUTION SAMPLING SYSTEM FOR EMISSIONS ANALYSIS

(75) Inventors: Zhili Gerald Liu, Madison, WI (US); Thaddeus Alan Swor, St. Paul, MN (US); Joseph Charles Lincoln, Madison, WI (US); Denise Christine Ford, Madison, WI (US)

(73) Assignee: Cummins Filtration IP Inc., Minneapolis, MN (US)

( * ) Notice: Subject to any disclaimer, the term of this patent is extended or adjusted under 35 U.S.C. 154(b) by 298 days.

(21) Appl. No.: 11/530,728

(22) Filed: Sep. 11, 2006

(65) Prior Publication Data
US 2008/0060456 A1   Mar. 13, 2008

(51) Int. Cl.
*G01N 1/22* (2006.01)
*G01N 1/26* (2006.01)
*G01N 1/38* (2006.01)

(52) U.S. Cl. ............... 73/863.12; 73/863.11; 73/863.31

(58) Field of Classification Search . 73/863.11–863.12, 73/863.23, 863.31, 863.33, 23.31
See application file for complete search history.

(56) References Cited

U.S. PATENT DOCUMENTS

| | | | |
|---|---|---|---|
| 3,457,787 A | 7/1969 | Maatsch et al. | |
| 3,853,008 A | 12/1974 | Hoffa et al. | |
| 5,058,440 A * | 10/1991 | Graze, Jr. | 73/863.83 |
| 5,806,282 A | 9/1998 | Hansen | |
| 6,928,890 B2 * | 8/2005 | Gehner et al. | 73/863 |
| 7,021,130 B2 | 4/2006 | Schmidt | 73/118.1 |
| 7,328,629 B2 | 2/2008 | Farthing et al. | |
| 7,363,828 B2 | 4/2008 | Liu | |
| 7,418,881 B2 | 9/2008 | Watson et al. | |
| 2006/0130599 A1 | 6/2006 | Graze, Jr. | |

FOREIGN PATENT DOCUMENTS

FR   2 670 893 A1   6/1992
JP   2006-226866 A   8/2006

OTHER PUBLICATIONS

U.S. Appl. No. 11/530,746, filed Sep. 2006, Liu et al.
U.S. Appl. No. 11/530,758, filed Sep. 2006, Liu et al.
http://www.sciencedaily.com/releases/2006/06/060625124445.htm, Jun. 25, 2006, 2 pages.

(Continued)

*Primary Examiner*—Thomas P Noland
(74) *Attorney, Agent, or Firm*—Hamre, Schumann, Mueller & Larson, P.C.; J. Bruce Schelkopf

(57) ABSTRACT

A system for sampling emission products from an emissions source, for example combustion engines including gasoline, diesel and natural gas engines, for subsequent measurement and analysis of the emission products. The system includes a dilution apparatus, a residence time chamber, a plurality of sampling probes within the residence time chamber, and a plurality of sampling trains connected to the sampling probes to take simultaneous representative emission samples for subsequent analysis. The system has particular use in quantifying chemical and toxic trace species from emissions sources. The results of the analysis can be used to formulate decisions on changes in engine design strategy, and can be used to determine the effectiveness of aftertreatment systems on the emissions source.

14 Claims, 9 Drawing Sheets

OTHER PUBLICATIONS

Hildeman et al., "Chemical Composition of Emissions from Urban Sources of Fine Organic Aerosol.", Environ. Sci. Technol., vol. 25, No. 4, 1991, pp. 744-759.

Hildeman et al., "A Dilution Stack Sampler For Collection of Organic Aerosol Emissions: Design, Characterization and Field Tests", Aerosol Science and Technology, vol. 10, 1989, pp. 193-204.

Kleeman et al., "Size and Composition Distribution of Fine Particulate Matter Emitted from Motor Vehicles", Environmental Science & Technology, vol. 34, No. 7, 2000, pp. 1132-1142, Feb. 19, 2000.

Kweon et al., "Detailed Chemical Composition and Particle Size Assessment of Diesel Engine Exhaust," SAE 2002-01-2670, Fall SAE Meeting 2002, pp. 1-13.

Liu et al., "Transient Performance of Diesel Particulate Filters as Measured by an Engine Exhaust Particle Size Spectrometer", 2005-01-0185, 2005 SAE International, pp. 1-14.

Liu et al., "Transient Analysis of Engine Nano-Particles Using a Fast-Scanning Differential Mobility Particle Analyzer", 2004-01-0971, 2004 SAE International, pp. 1-10.

Liu et al., "Diesel Particulate Filters: Trends and Implications of Particle Size Distribution Measurement", 2003-01-0046, 2003 Society of Automotive Engineers, Inc., pp. 1-14.

MacGibbon et al., "The Effect of Thermophoresis on Particle Deposition in a Tungsten Low Pressure Chemical Vapor Deposition Reactor", Journal of The Electrochemical Society, vol. 146, No. 8, 1999, pp. 2901-2905.

Schauer et al., "Measurement of Emissions from Air Pollution Sources. 2. $C_1$ through $C_{30}$ Organic Compounds from Medium Duty Diesel Trucks", Environmental Science & Technology, vol. 33, No. 10, 1999, pp. 1578-1587.

"Performance Standards and Test Procedures for Automatic Isokinetic Samplers", Environment Agency, Version 1, Sep. 2005, pp. 1-12.

Office Action issued Dec. 23, 2008 in related U.S. Appl. No. 11/530,746.

Office Action issued Nov. 26, 2008 in related U.S. Appl. No. 11/530,758.

* cited by examiner

SOURCE DILUTION SAMPLING SYSTEM FOR EMISSIONS ANALYSIS

FIELD

A system for sampling emission products from an emissions source, for example combustion engines including gasoline engines, diesel engines, and natural gas engines for subsequent measurement and analysis of the emission products.

BACKGROUND

Emissions of pollutant chemicals have increased orders of magnitudes in the past 100 years due primarily to anthropogenic releases associated with industrial, agricultural, domestic, and recreational activity. Current research indicates that there are very strong correlations between the increase in these emissions and an overall increase in atmospheric temperatures (i.e. global warming) and an increased number of Category 4 and 5 hurricanes per annum. Furthermore, it is believed that ambient particulate matter in aerosol phase may include potentially toxic components. Researchers also believe that particulate matter and gases from industrial activities and vehicles may cause various health problems, such as asthma. These correlations between emissions of pollutant chemicals and the negative impact on environment and human health has led to more stringent worldwide emission standards for automobiles and other vehicles, as well as power plants, mines, and other industries.

In the United States, emission standards are set by the Environmental Protection Agency (EPA) as well as state governments (e.g. California Air Resource Board (CARB)). As of this writing, all new vehicles sold in the United States must meet the EPA's "Tier 1" emission standard. A more stringent standard, "Tier 2," is being phased in for automobiles and should be completed by 2009. For diesel engines, on-road trucks and other vehicles will be required to meet more stringent standards by 2010 and off-road vehicles such as construction vehicles will be subject to Tier IV regulations. Accordingly, attaining ultra low emissions has become a top priority for combustion researchers as federal and state regulations continuously reduce the allowable levels of pollutants that can be discharged by engines, power plants, and other industrial processes.

In order to meet the emission standards of today and the future, researchers have made, and are continually striving to make, improvements to combustion engines, for example heavy duty diesel engines, gas combustion engines, power-generating gas turbines, and the like, and other emission sources. In addition to these developments, researchers are endeavoring for better methods and devices of measuring smaller particulate matter and low level gases and quantifying the chemical compositions of emissions.

Generally, chemical composition analysis of fine particulate matter, gases, and volatile and semi-volatile organic compounds from emissions sources consists of three major steps: (1) Representative conditioning and sampling; (2) Chemical analysis; and (3) Data analysis and explanation. The effective accuracies of Steps (2) and (3) are both dependent on step (1). For without an accurate and precise sampling procedure, no analysis of that sample could be said to represent valid data. Accordingly, without valid analysis, a full and complete explanation of the sample would not be available.

A conventional system for assessing particle mass and quantifying chemical composition of emission gases mixes emission gas with filtered air in a mixing chamber. The conventional system is illustrated in FIG. 1, and includes a sampling port 2 that feeds exhaust gases to a diluter 4, forming the mixing chamber, where the exhaust gases are diluted with the filtered air. The diluted gas mixture is then sampled by a sampling train 6. However, this system has many well recognized disadvantages. First, the partial/full/partial dilution sampling system in this conventional system would introduce more errors than a full/partial/full system. Second, the conventional system allows only for assessment of single type of compound. Accordingly, multiple sample runs are required to detect each of the chemical compounds necessary for a full compound assessment (particulate matter, volatile organics, semi-volatile organics, and gases, etc.) Furthermore, these measurements are made with different samples each time, and may add to inherent errors that are unavoidable to this system. These errors may lead to inaccurate measurements and quantification of data.

Work at the University of Wisconsin-Madison attempted to improve the conventional system. University of Wisconsin scientists used a device called an "augmented sampling system" to study the chemical composition and to assess particle size of diesel engine exhaust. See Chol-Burn Kweon, David E. Foster, James J. Schauer, and Shusuke Okada, "Detailed Chemical Composition and Particle Size Assessment of Diesel Engine Exhaust" SAE 2002-01-2670, Fall SAE Meeting 2002. The "augmented sampling system" disclosed by Kweon et al includes a secondary dilution tunnel for the diesel exhaust and a residence time chamber with radial sampling ports near the base of the residence time chamber. The secondary dilution tunnel of the augmented sampling system mixes filtered air with an emission gas sample without regard to temperature gradient between the surface of the dilution tunnel and the emission gas. This may lead to a high degree of particle loss and accordingly less accurate sampling due to thermophoresis.

Thermophoresis, or Ludwig-Soret effect, is thought to be related to Brownian movement biased by a temperature gradient. The thermophoretic force is a force that arises from asymmetrical interactions of a particle with the surrounding gas molecules due to a temperature gradient. Generally, a particle is repelled from a hotter surface and attracted to a cooler surface. Thus, as emission particles travel through a sampling system, cooler surface temperature of the system as compared to the emission gas would lead to greater thermophoretic force on the emission particles.

In the Kweon et al. augmented sampling system, the residence time chamber is heated to reduce thermophoresis. However, the heated residence time chamber is likely to fail in achieving realistic atmospheric conditions, as the addition of heat may underestimate the particulate matter emissions due to the reduced effects of nucleation and condensation and may also affect secondary reactions of volatile organic compounds and semi-volatile organic compounds and formation of secondary organic compounds.

A system that allows more accurate and precise sampling of emission products is needed, thereby contributing to better measurement and analysis of the emission products.

SUMMARY

A system is provided for sampling emission products from an emissions source, for example combustion engines including gasoline, diesel and natural gas engines, for subsequent measurement and analysis of the emission products. The system has particular use in quantifying particle size distributions and chemical species from low emissions sources. The results of the analysis can be used to formulate decisions on changes in engine design strategy, and can be used to determine the effectiveness of aftertreatment systems on the emissions source.

The system uses a full/partial/full approach and includes an isokinetic sampling nozzle, a dilution apparatus, a residence time chamber, a plurality of sampling probes within the residence time chamber, and a plurality of sampling trains connected to the sampling probes to take simultaneous representative emission samples for subsequent analysis.

The dilution apparatus is designed to be thermophoretic-resistant to reduce the thermophoretic force on emission particles, thereby reducing particulate matter losses. In addition, the dilution apparatus is designed to simulate atmospheric dilution, mixing and cooling processes, enabling the sampled gas and the dilution gas to thoroughly mix and cool to ambient temperature, allowing gas-phase organics in the sampled gas to nucleate and condense to their usual aerosol phase.

The residence time chamber is designed to provide sufficient time for gas-to-particle conversion, which involves the diffusion limited transport of supersaturated vapor onto existing particles. Preferably, the residence time chamber is designed to provide at least 30 seconds of residence time. During this time, the sample flow and concentrations within the residence time chamber also become uniformly distributed before entering the sampling probes.

The sampling probes are aligned coaxial to the flow direction within the residence time chamber (i.e. isoaxial) with the inlets of the probes facing into the direction of flow. This improves collection of the emission samples since the samples do not need to turn sharp corners to enter the probes. The plurality of sampling trains connected to the sampling probes permit the simultaneous sampling of different materials, including, but not limited to, volatile and semi-volatile organic, gas-phase, and particulate matter samples.

A method of sampling emission products from an emissions source is also provided. The method includes directing a sample of a gas stream from the emissions source into a dilution apparatus. In the dilution apparatus, heat is exchanged between the gas stream sample and a dilution gas to cool the gas stream sample, and thereafter the dilution gas is introduced into the gas stream sample to mix with the gas stream sample. The gas mixture is then directed to a residence time chamber, and a sample of the gas mixture is taken from the residence time chamber through a sampling probe having an inlet that is substantially parallel to a direction of flow of the gas mixture within the residence time chamber.

In one embodiment, a system for sampling emission products from an emissions source comprises a dilution apparatus connected to a sampling probe to receive a gas stream sample. The dilution apparatus includes an inlet through which the gas stream sample enters, a dilution gas inlet through which dilution gas enters the dilution apparatus, and an exit through which a mixture of dilution gas and the gas stream sample exits the dilution apparatus. A dilution gas source is connected to the dilution gas inlet of the dilution apparatus for supplying dilution gas. A residence time chamber is connected to the dilution apparatus and receives therefrom the gas mixture. The residence time chamber includes a plurality of isoaxial sampling probes disposed inside the chamber. Further, a sampling train is connected to each of the isoaxial sampling probes.

In another embodiment, a system for sampling emission products from an emissions source comprises a dilution apparatus connected to a sampling probe to receive a gas stream sample. The dilution apparatus includes an inlet through which the gas stream sample enters, a dilution gas inlet through which dilution gas enters the dilution apparatus, an exit through which a mixture of dilution gas and the gas stream sample exits the dilution apparatus, and a plurality of holes axially spaced from the dilution gas inlet which allow introduction of the dilution gas into the gas stream sample. In addition, the dilution apparatus is configured so that the dilution gas exchanges heat with the gas stream sample prior to being mixed with the gas stream sample. A dilution gas source connected to the dilution gas inlet of the dilution apparatus, and a residence time chamber that is connected to the dilution apparatus receives therefrom the gas mixture. Further, a plurality of sampling trains are connected to the residence time chamber.

In yet another embodiment, a system for sampling emission products from an emissions source comprises a dilution apparatus connected to a sampling probe to receive a gas stream sample. The dilution apparatus includes a longitudinal axis, an inlet through which the gas stream sample enters, a dilution gas inlet through which dilution gas enters the dilution apparatus, and an exit through which a mixture of dilution gas and the gas stream sample exits the dilution apparatus. A dilution gas source is connected to the dilution gas inlet of the dilution apparatus, and a residence time chamber is connected to the dilution apparatus and receives therefrom the gas mixture. The residence time chamber includes a longitudinal axis that is substantially perpendicular to the longitudinal axis of the dilution apparatus. Further, a plurality of sampling trains are connected to the residence time chamber.

DETAILED DESCRIPTION

Figure 1:
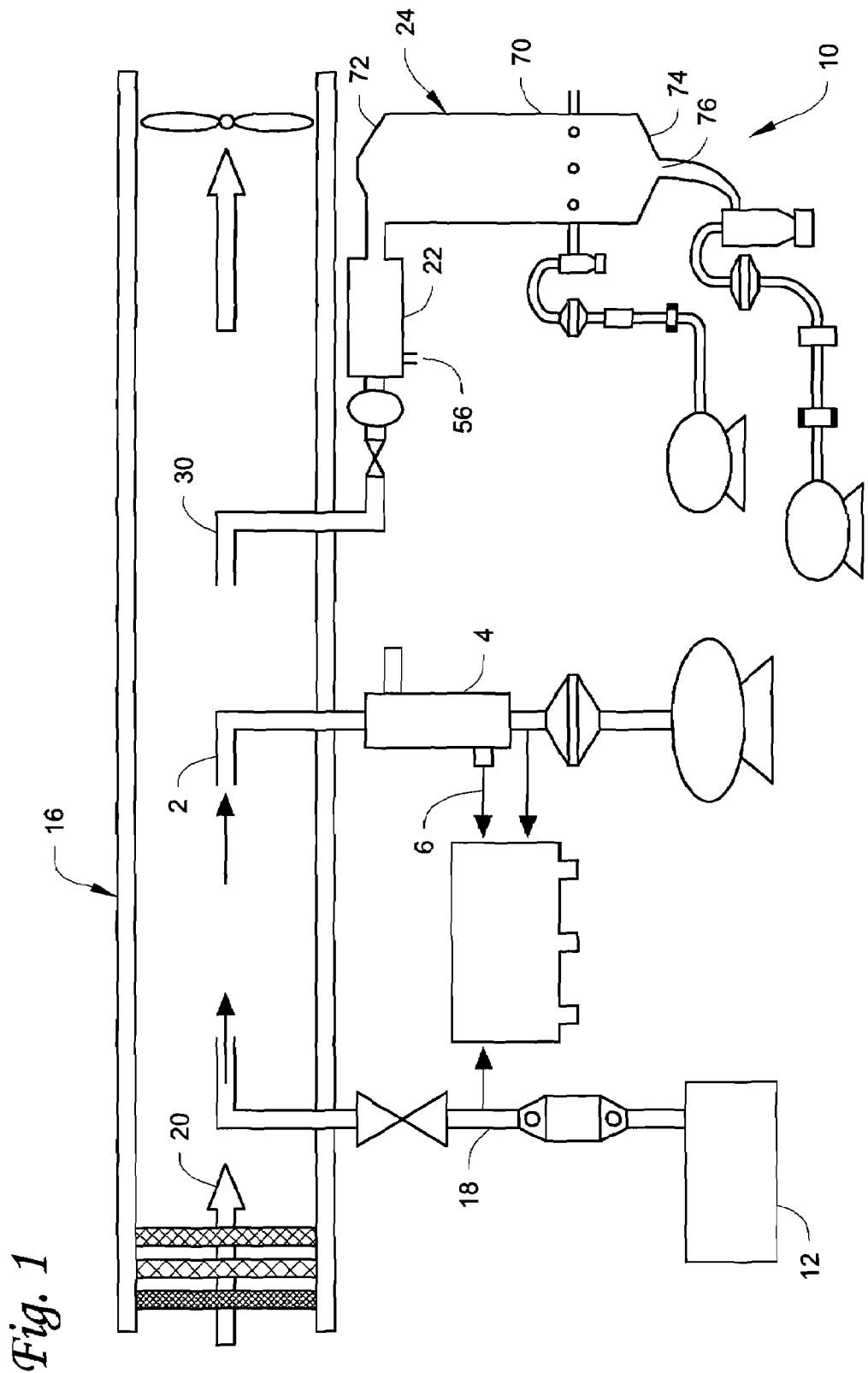
FIG. 1 illustrates a sampling system according to the invention connected to a dilution tunnel for sampling emissions from an engine.

With reference to FIG. 1, a system 10 for sampling emission products from an emissions source 12 is illustrated. The system 10 is constructed to simultaneously sample a number of different emissions products emitted from the emissions source 12. The samples can then be analyzed to permit chemical characterization of the emissions products with respect to air toxics.

The system 10 will be described herein as being applied to the sampling and chemical characterization of diesel emission exhaust from an emissions source 12 in the form of a diesel engine. However, the concepts described herein can be used to great advantage in sampling a number of other types of gases from a number of other types of emissions sources, both stationary and mobile. Examples of other types of gases includes, but is not limited to, gas combustion engine exhaust, turbine engine exhaust, and atmospheric gas. Examples of other types of emissions sources includes, but is not limited to, gas combustion engines, turbine engines, power plants, manufacturing plants, exhaust stacks, etc.

As shown in FIG. 1, the entire exhaust from the engine 12 is ducted to a dilution tunnel 16 through suitable piping 18. Filtered dilution air 20 is introduced into the tunnel upstream of the discharge for the engine exhaust, with the dilution air 20 then mixing with the engine exhaust in the tunnel 16 to dilute and cool the exhaust gas.

System

Figure 2:
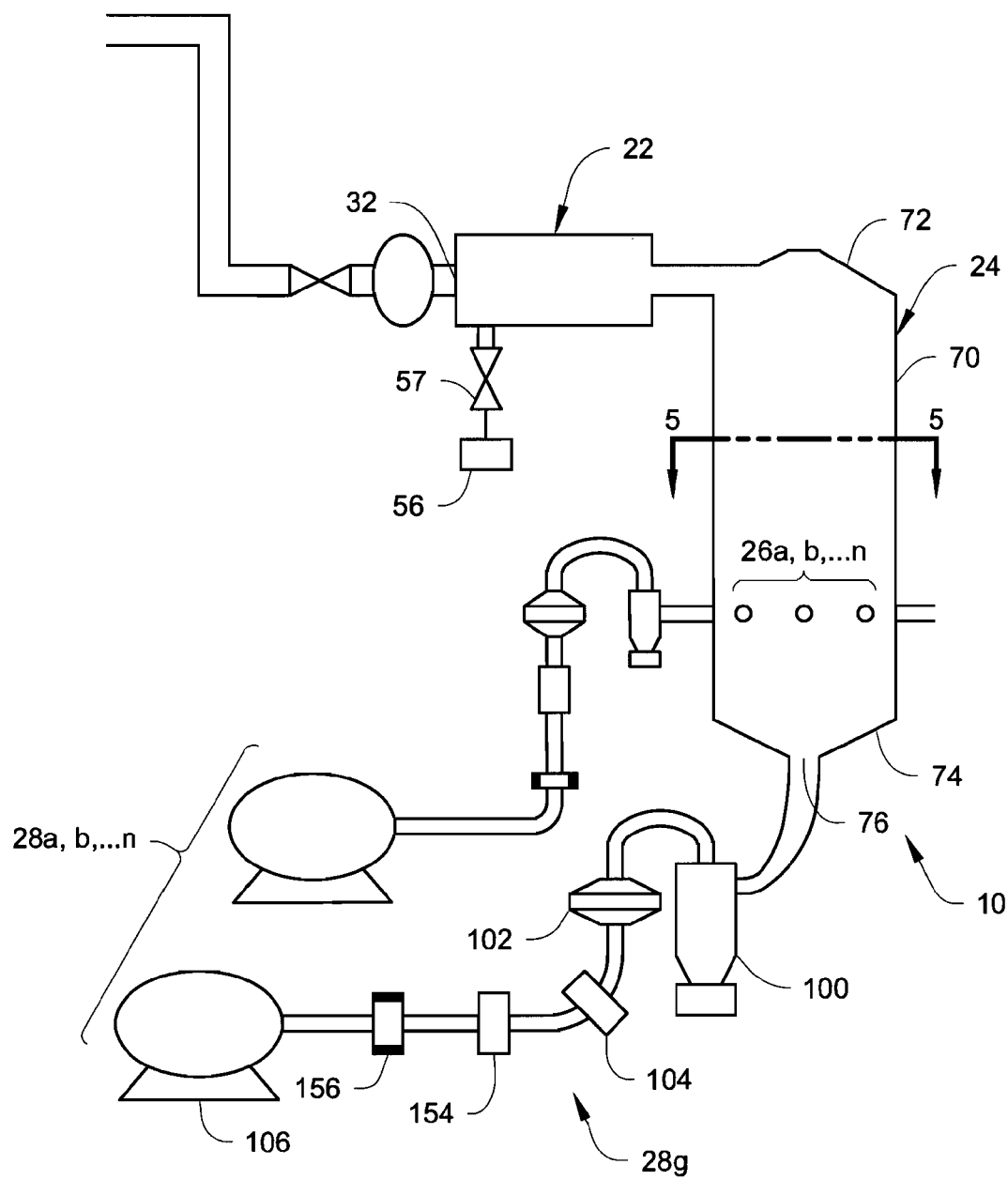
FIG. 2 illustrates the sampling system separate from the dilution tunnel.

With reference to FIGS. 1-2, the system 10 includes a dilution apparatus 22, a residence time chamber 24, a plurality of sampling probes 26a, b, ... n (FIGS. 7 and 8) within the residence time chamber, and a plurality of sampling trains 28a, b, ... n (FIGS. 9 and 10) connected to the sampling probes to take simultaneous representative emission samples for subsequent analysis.

The dilution apparatus 22 is connected to a sampling probe 30 that extends into the dilution tunnel 16. The probe 30 collects a gas stream sample from the engine 12 and directs the gas stream sample to the dilution apparatus 22. The inlet of the probe 30 is preferably iso-kinetic and positioned proximate the center of the dilution tunnel 16 to minimize boundary effects caused by the walls of the tunnel 16. In the dilution apparatus 22, the sampled gas is diluted with dilution gas, cooled to ambient temperature, and thoroughly mixed with the dilution gas.

The result is a full/partial/full dilution scheme, where the entire exhaust stream is initially diluted within the dilution tunnel 16, a portion of the exhaust stream is sampled by the sampling probe 30, and the entire portion of the gas sample is then diluted in the dilution apparatus. This full/partial/full dilution scheme is an improvement over conventional partial/full/partial dilution schemes, which direct only a portion of the exhaust stream into the dilution tunnel 16. As a result, the number of particles seen in resulting samples is low compared to a full/partial/full dilution scheme.

The gas mixture is then fed to the residence time chamber 24 which is designed to provide sufficient time for gas-to-particle conversion, which involves the diffusion limited transport of supersaturated vapor onto existing particles. The gas flow also becomes uniformly distributed before entering the sampling probes 26a, b, ... n. The samples probes 26a, b, ... n simultaneously collect multiple samples of the gas mixture and feed the samples to the sampling trains 28a, b, ... n which are constructed to take various samples of the gas. Preferably, the sampling trains are configured to sample unregulated chemical species within the gas samples, for example volatile and semi-volatile organics, gas-phase compounds, and particulate matter.

The components of the system 10 are preferably made of inert materials, including, but not limited to, stainless steel, plastic or polymer materials, such as TEFLON, and plastic or polymer coated aluminum such as TEFLON-coated aluminum. In addition, the use of electrically non-chargeable materials, such as 304, 316 and 316L stainless steels, can also be used to reduce electrostatic deposition of charged particles that are typically polarized during combustion processes. In addition, the system 10 is preferably devoid of materials, for example oils, greases, rubbers and the like, that could outgas organics to avoid contamination of the gas stream and gas samples.

Further, the system 10 is preferably configured to minimize vapor and particulate losses. For example, the system is designed to promote smooth flow transitions within the system 10.

Dilution Apparatus

With reference to FIGS. 1-4, the dilution apparatus 22 is designed to be thermophoretic-resistant to reduce the thermophoretic force on emission particles, thereby reducing particulate matter losses. In addition, the dilution apparatus 22 preferably simulates atmospheric dilution, mixing and cooling processes, enabling the sampled gas and the dilution gas to thoroughly mix and cool to ambient temperature, allowing gas-phase organics in the sampled gas to nucleate and condense to their usual aerosol phase.

Figure 3:
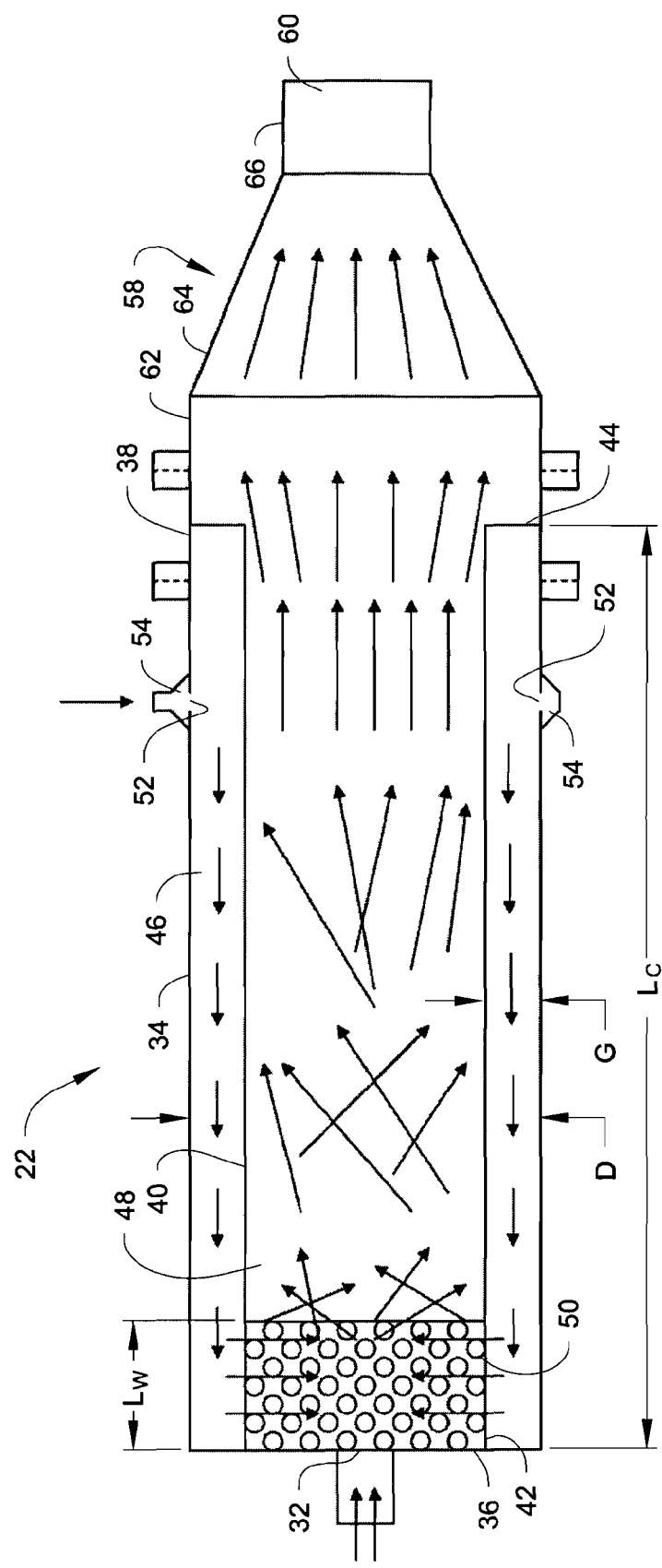
FIG. 3 is a cross-sectional view of the dilution apparatus taken along the longitudinal axis thereof.
Figure 4:
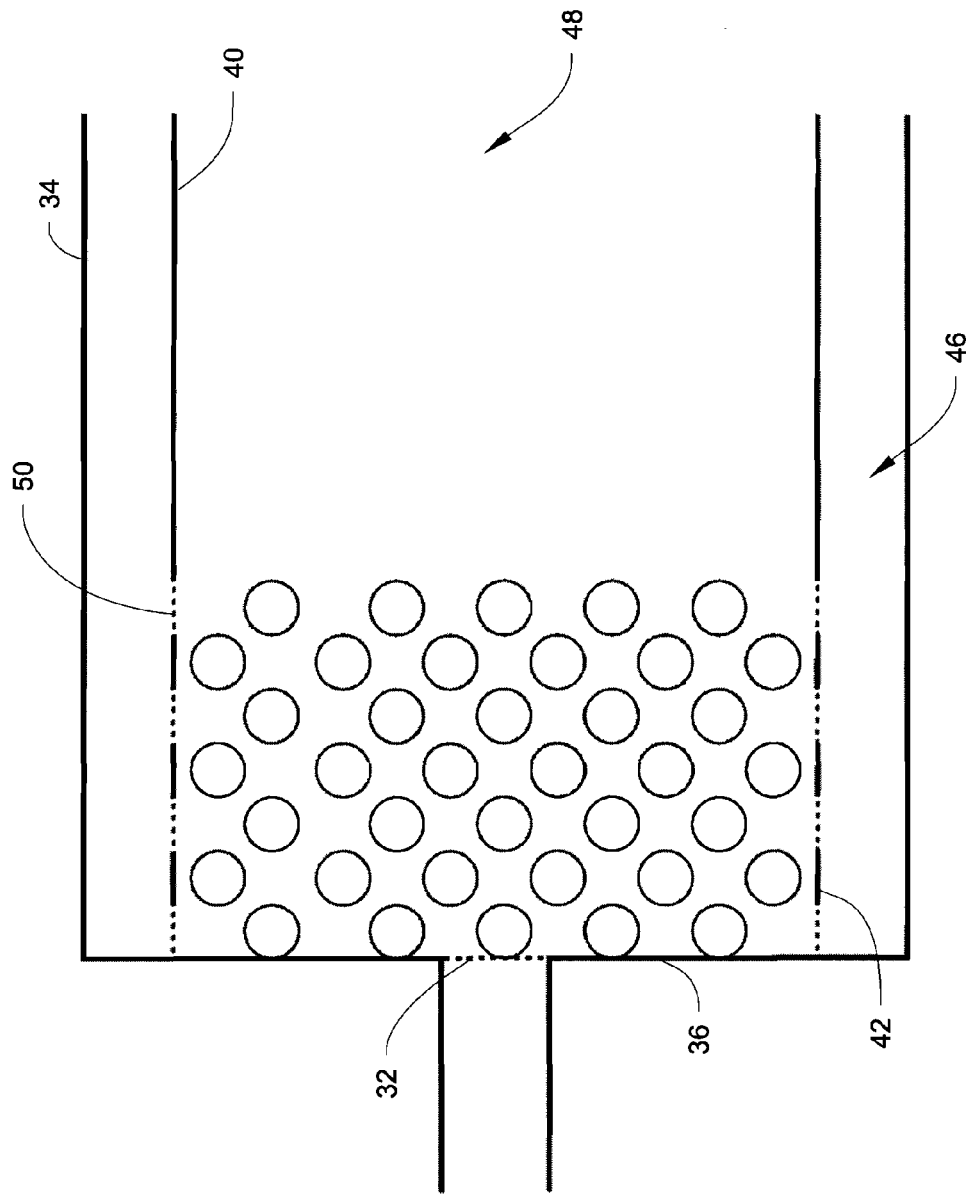
FIG. 4 is a detailed view of the perforations in the inner tube.

The sampled gas collected by the sampling probe 30 enters the dilution apparatus 22 through an inlet 32. As shown in FIGS. 3-4, the dilution apparatus 22 has a cylindrical housing 34 with a first end 36 that includes the inlet 32, a second end 38 and an interior space. An inner cylindrical wall 40 is located concentrically with the housing 34, with the cylindrical wall 40 having a first end 42 adjacent the first end 36 of the housing and a second end 44 adjacent the second end 38 of the housing. The cylindrical wall 40 divides the interior space into a static pressure chamber 46 defined between the housing 34 and the wall 40 and that extends generally from the first end 42 of the wall to the second end 44 of the wall 40, and a mixing chamber 48 that extends generally from the first end of the wall to the second end of the wall.

The wall 40 has circumferentially and axially distributed perforations 50 near the first end 42 thereof that place the static pressure chamber 46 in communication with the mixing chamber 48. In addition, the housing 34 has a plurality of evenly, circumferentially spaced inlet ports 52 near the second end 44 thereof that open into the static pressure chamber 46 for introducing a dilution gas into the static pressure chamber 46. The inlets ports 52 communicate with a plenum 54 defined around the circumference of the housing 34, and dilution gas is fed to the plenum 54 from a dilution gas source 56. If desired, the dilution gas source 56 can be a source of over-pressure, such as a compressor, and a regulator 57, such as a valve, can be used to regulate the flow of dilution gas into the dilution apparatus. The gas source 57 and/or regulator 57 can be used to control the amount of dilution gas that is fed to the dilution apparatus, thereby changing the dilution ratio of the gas stream sample and the dilution gas.

In use, the sampled gas enters the mixing chamber 48 of the dilution apparatus through the inlet 32 as shown by the arrows in FIG. 3. In addition, dilution gas is introduced into the static pressure chamber 46 through the inlets ports 52. As the dilution gas flows toward the first end 42 as shown by the arrows in FIG. 3, it exchanges heat with the sampled gas in the mixing chamber 48. In an alternative embodiment, insulation material can be provided on the wall 40 to keep the inner part of the wall 40 the same temperature as the sample gas, thereby lowering the effect of thermophoresis.

Once the dilution gas reaches the perforations 50, it flows radially inward into the mixing chamber 48 to mix with the sampled gas. FIG. 3 illustrates the flow of dilution air into the mixing chamber 48. The perforation holes 50 create jets of dilution air that impinge upon the sampled gas to create turbulent mixing with the sampled gas. Preferably, the perforation holes 50 are configured to generally evenly distribute the dilution gas into the mixing chamber. In the illustrated embodiment, the holes 50 are circumferentially and axially evenly spaced about the wall 40. Mixing of the dilution gas and the sampled gas also cools the sampled gas.

The dilution gas is at a temperature lower than the sampled gas, so that the sampled gas is cooled through heat exchange with the static pressure chamber and as a result of mixing with the dilution gas, allowing gas-phase organics in the sampled gas to nucleate and condense to their usual aerosol phase in the atmosphere. Preferably, the sampled gas is cooled to a temperature that is at least within 5° C. of ambient temperature by the time the mixture of sampled gas and dilution gas reaches the exit of the dilution apparatus. More preferably, the sampled gas is cooled to ambient temperature by the time the mixture of sampled gas and dilution gas reaches the exit of the dilution apparatus. In certain embodiments, the sampled gas can be cooled to a temperature below ambient temperature.

In addition, because the sampled gas is cooled to at or near ambient temperature, temperature differences between the exterior of the apparatus 22 and the gas mixture within the mixing chamber 48 is reduced, thereby reducing the thermophoretic force acting on particles in the flow. This reduces particle loss as the gas sample flows through the dilution apparatus 22.

The number and size of the perforation holes 50 is chosen based on the gas being sampled, the gas temperature, and the desired dilution rate. For diesel engine exhaust, the holes can provide between 20% to 80% porosity, have diameters ranging from about 0.125 inch to about 0.5 inch, and extend over a length $L_w$ of the wall 40 ranging from about 0.06 inches to about 15 inches (FIG. 3). In addition, the dimensions of the dilution apparatus 22 are chosen based on the temperature of the sampled gas and the flow rate. With reference to FIG. 3, for diesel engine exhaust, the length $L_c$ of the mixing chamber 48 can vary between 18.0 inches to 63.0 inches, the housing can have a diameter D between 3.0 inches and 10.5 inches, and the gap G defining the static pressure chamber between the wall 40 and the housing 34 can vary between 0.2 inches and 2.0 inches.

As shown in FIG. 3, a reducing cone 58 is connected to the end of the housing 34 and defines an exit 60 for the mixture of sampled gas and dilution gas from the dilution apparatus 22. The reducing cone 58 includes a first constant diameter section 62 that connects to the housing 34, a tapered section 64 that reduces in diameter to reduce the diameter of the flow path, and a second constant diameter section 66 that defines the exit 60 and which is directly connected to the residence time chamber 24. The reducing cone 58 helps to provide a smooth flow transition of the gas mixture from the dilution apparatus 22 to the residence time chamber 24.

Further details on the dilution apparatus 22 can be found in copending U.S. patent application Ser. No. 11/530,758, filed on Sep. 11, 2006, and titled Thermophoretic-Resistant Gas Dilution Apparatus For Use in Emissions Analysis, which application is incorporated herein by reference.

Residence Time Chamber

The residence time chamber 24 is best illustrated in FIGS. 1, 2, 5 and 6. The chamber 24 includes a housing 70 having a first end 72 and a second end 74. In the illustrated embodiment, the housing 70 is oriented generally vertically so that the longitudinal axis of the housing 70 is oriented vertically and generally perpendicular to the longitudinal axis of the dilution apparatus 22 which is disposed generally horizontally.

The housing 70 is connected to the reducing cone 58 of the dilution apparatus 22 at the first end 72. Preferably, the first end 72 is in the form of a conical section, with the cone opening or facing downward. The gas mixture is received into the conical section 72, with the conical section helping to promote a smooth flow transition of the gas mixture from the dilution apparatus to the residence time chamber. Likewise, the second end 74 is in the form of a conical section, with the cone opening or facing upward. The conical section 74 helps to promote a smooth flow transition from the residence time chamber to an exit port 76 located at the bottom of the conical section 74.

The housing 70, except for the conical sections 72, 74, is generally cylindrical and has a constant diameter from the conical section 72 to the conical section 74. The housing 70 provides sufficient time for gas-to-particle conversion within the gas mixture, and allows the gas flow to become uniformly distributed. Preferably, the housing 70 provides at least 30 seconds of residence time for the gas flow from the time the gas flow enters the housing 70 to the time the gas flow reaches and enters one of the sampling probes. A residence time of 30 seconds can be provided by a housing 70 with a height of about 57 inches and a diameter of about 12.0 inches.

Figure 5:
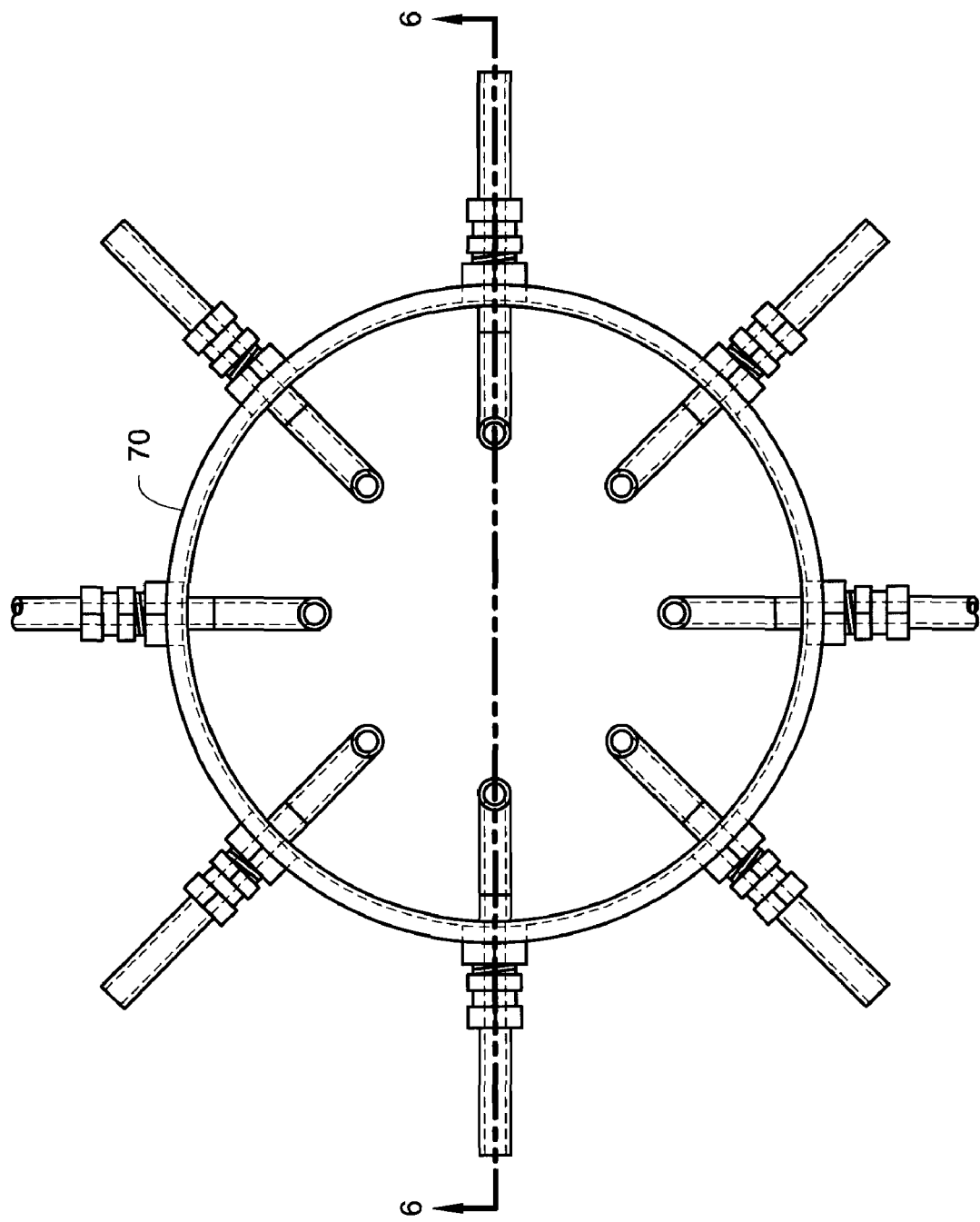
FIG. 5 is a cross-sectional view of the residence time chamber taken along line 5-5 in FIG. 2.
Figure 6:
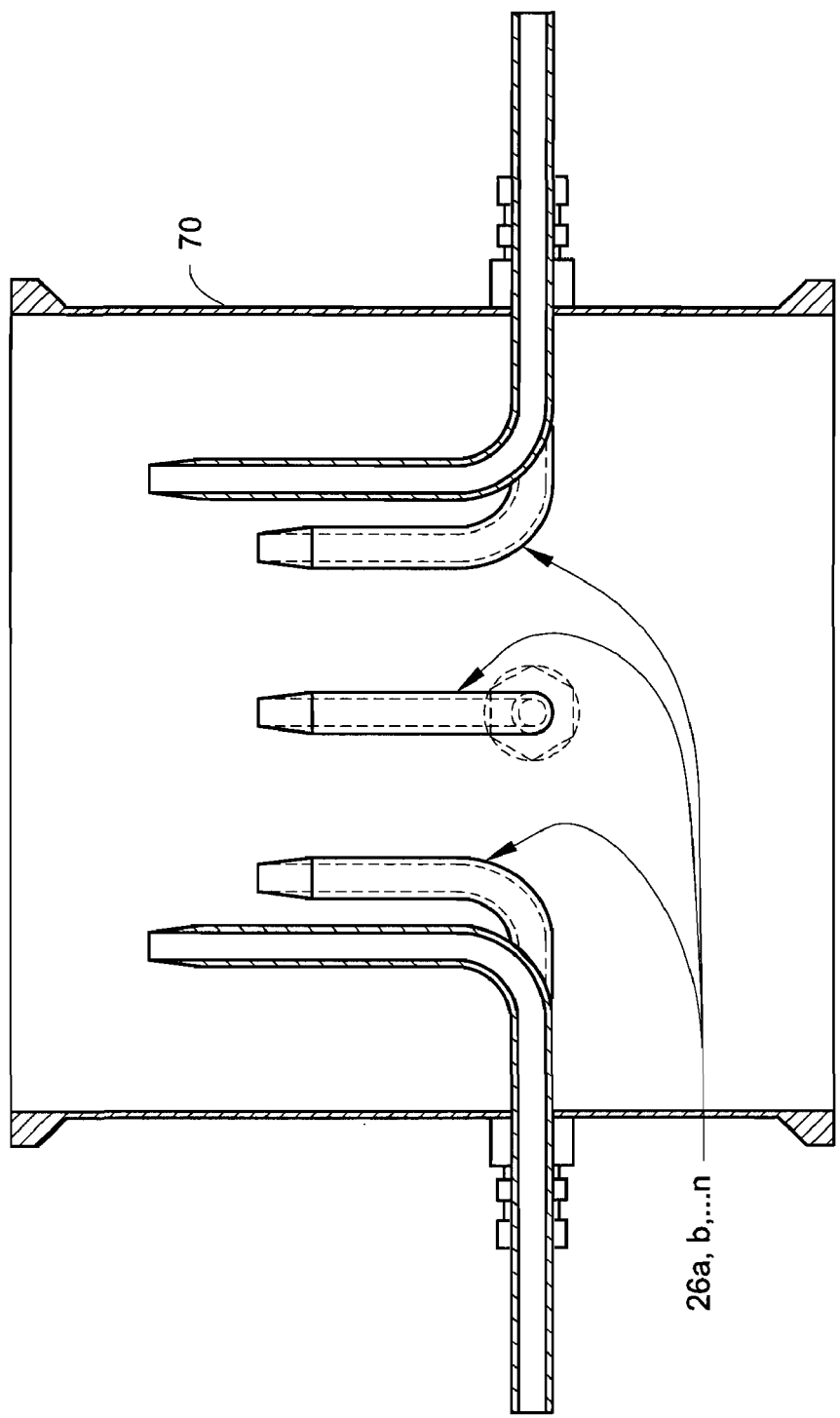
FIG. 6 is a cross-sectional view taken along line 6-6 in FIG. 5.

As shown in FIGS. 5 and 6, the sampling probes 26a, b, . . . n are disposed inside of the housing 70 to simultaneously collect multiple samples of the gas mixture and feed each sample to the sampling train 28a, b, . . . n. The sampling probes are aligned coaxial to the flow direction to achieve isoaxial and isokinetic sampling. In the illustrated embodiment, 8 sampling probes are provided, with each of the sampling probes 26a, b, . . . n extending upward with the inlets to the probes facing upward toward the oncoming flow. To avoid boundary flow effects of the housing wall, the sampling probes are preferably spaced inwardly from the housing wall. Because the sampling probes are isoaxial and face upward toward the oncoming flow, sampling is improved because the sampled flow does not need to turn sharp corners to enter the probes.

Further details on the residence time chamber and the sampling probes can be found in copending U.S. patent application Ser. No. 11/530,746, filed on Sep. 11, 2006, and titled Residence Time Chamber and Sampling Apparatus, which application is incorporated herein by reference.

Sampling Trains

The gas samples entering the sampling probes 26a, b, . . . n are directed to the sampling trains 28a, b, . . . n. The sampling trains can be configured to take samples of any kind of matter within the gas samples. Preferably, the sampling trains are configured to sample unregulated chemical species within the gas samples, for example volatile and semi-volatile organics, gas-phase compounds, and particulate matter.

Figure 7:
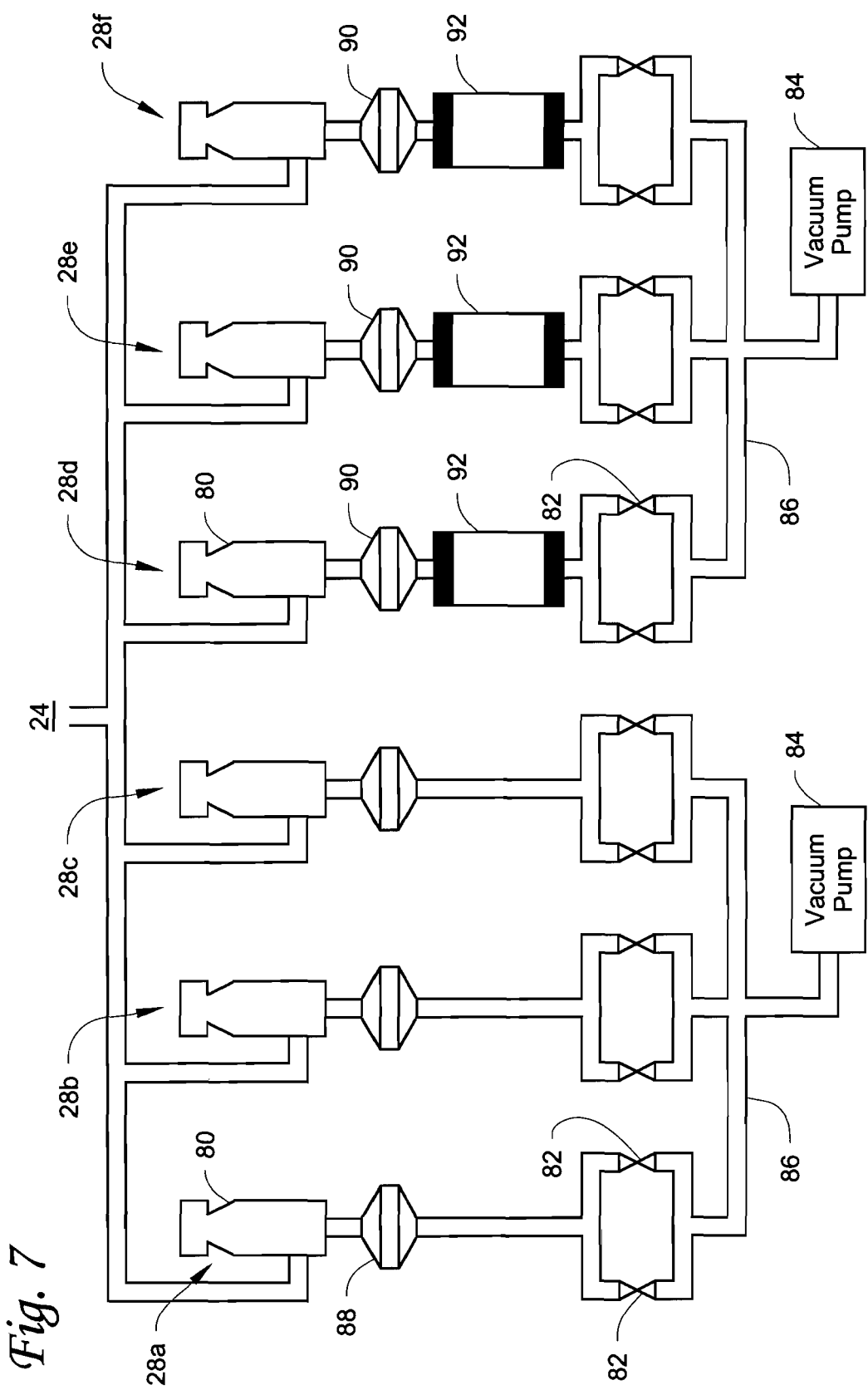
FIG. 7 illustrates exemplary flow trains connected to the residence time chamber.
Figure 8:
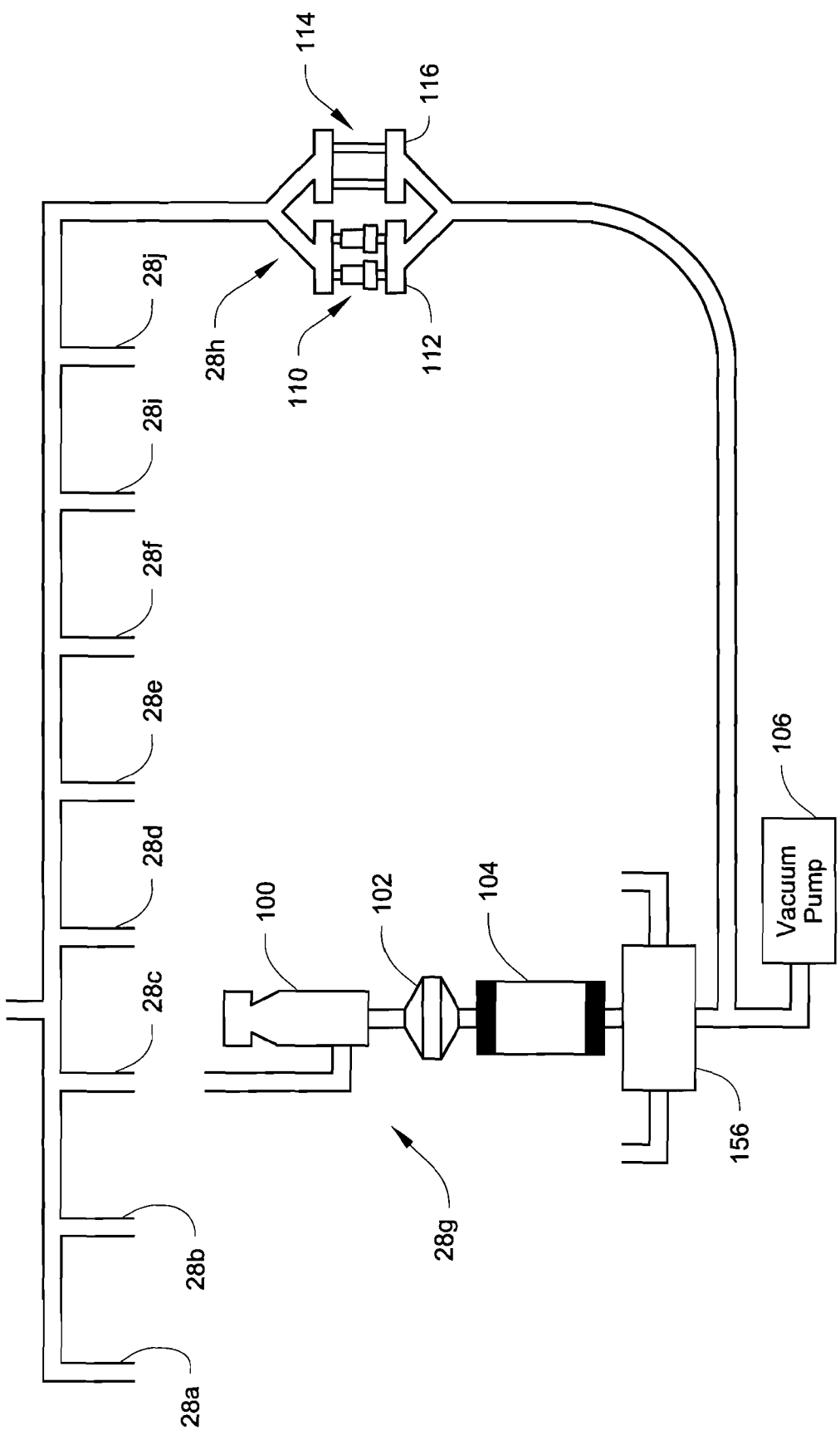
FIG. 8 illustrates additional exemplary flow trains connected to the residence time chamber.

Examples of suitable sampling trains are illustrated in FIGS. 7 and 8. As shown in FIG. 7, sampling trains 28a, 28b, 28c each begin with a PM2.5 cyclone separator 80 that can be operated at a flow rate of 16.7 liters/min (lpm) for removing particles that are about 2.5 microns and above. Flow through the trains 28a, 28b, 28c is controlled by downstream critical flow orifices 82 in series with a rotary vacuum pump 84 via a manifold 86. A rotameter prior to each critical flow orifice can be used to monitor the flow rate. A filter 88, for example a two stage TEFLON membrane filter, is disposed after the separator 80 to filter out material from the sampled gas. The filters 88 can then be analyzed for collected material. When the filters 88 are TEFLON membrane filters, analysis can be conducted for total mass, particulate matter sulfate ions, and particulate matter trace elemental composition.

The sampling trains 28d, 28e, 28f illustrated in FIG. 7 are similar to the sampling trains 28a, 28b, 28c. However, the illustrated trains 28d, 28e, 28f utilize a filter 90, preferably a two stage quartz fiber filter, in series with a polyurethane foam (PUF) cartridge 92. An adsorption material substrate, such as an XAD™ substrate, could be used in place of the PUF cartridge in the case of higher flow rates. When the filters 90 are quartz filters, particle-phase organic compounds can be collected to analyze for particulate matter organics, nitro-PAH particulate matter, and particulate matter hydrocarbon distribution. In the case of PUF cartridges, semi-volatile organic compounds can be collected to analyze for semi-volatile organic compounds, semi-volatile nitro-PAH, and semivolatile hydrocarbon distribution.

With reference to FIG. 8, a sampling train 28g that is designed for high flow samples is illustrated. The sampling train 28g is connected to the exit port 76 at the bottom of the conical section 74. The sampling train 28g is not connected to a sampling probe. Instead, the sampling train samples the remainder of the gas flow that is not sampled by the sampling probes as the gas flow remainder exits through the bottom of the residence time chamber 24. The train 28g includes a PM2.5 cyclone separator 100 that can be operated at a flow rate of 92 liters/min (lpm) for removing particles that are about 2.5 microns and above, followed in series by a filter 102, for example a quartz filter, a PUF cartridge 104 (or XAD substrate), critical flow orifices 156, and a rotary vacuum pump 106. This kind of sampling train 28g is suitable for use in collecting samples for polycyclic aromatic hydrocarbon analysis from low emission sources. The sampling train 28g can also include a flow meter 154, shown in FIGS. 1 and 2.

FIG. 8 also illustrates a gaseous sampling train 28h which can be run in parallel to the sampling trains 28a-f. The sampling train 28h includes two Dinitrophenyl-Hydrazine (DNPH) cartridges 110 arranged in parallel to collect samples which are subsequently analyzed for carbonyl species. The cartridges 110 can have different flow rates, for example about 1.5 lpm and about 0.3 lpm. The flow rate can be controlled by critical flow orifices 112 in series with the rotary vacuum pump 106. In addition, the train 28h can include two volatile organic compound (VOC) tubes 114 arranged parallel to the DNPH cartridges to collect samples for hydrocarbon speciation. The flow rates through the VOC tubes 114 can range from about 10 standard cubic centimeter (SCCM) to 50 SCCM, controlled by two separate mass flow controllers 116 in series with the vacuum pump 106. The mass flow controllers 116 can also be used to collect mass flow, volumetric flow, pressure, and temperature data. If desired, one or two filters prior to the DNPH cartridges 110 and VOC tubes 114 can be used to collect large particles.

An additional sampling train 28i can be used to measure particle size distributions for steady-state and transient operations. In addition, a sampling train 28j can include temperature, humidity, and pressure sensors to monitor the residence time chamber conditions.

Other types of sampling trains for collecting other types of materials within the sampled gas can be used. The sampling trains described herein are intended to be exemplary and not intended to be limiting.

Further details on the sampling trains can be found in U.S. patent application Ser. No. 11/530,746, filed on Sep. 11, 2006, and titled Residence Time Chamber and Sampling Apparatus.

Figure 9:
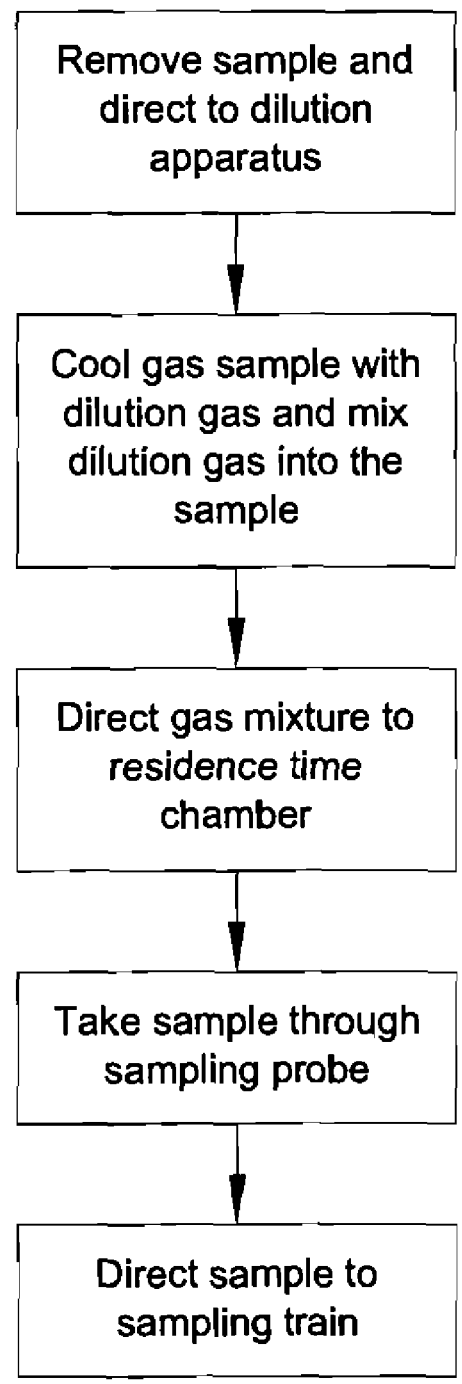
FIG. 9 is a flow chart of an exemplary sampling method of the invention.

The method of operation of the system 10 and of sampling exhaust gas from the engine 12 is apparent from the preceding description. With reference to FIG. 9, a sample of the exhaust gas from the engine is initially directed into the dilution apparatus 22, through the sampling probe 30. Next, in the dilution apparatus, the gas sample is cooled by the dilution gas and the dilution gas and the gas sample are mixed. The gas mixture is then directed to the residence time chamber, and a sample, preferably a plurality of simultaneous samples, of the gas mixture is taken from the residence time chamber through a sampling probe having an inlet substantially parallel to a direction of flow of the gas mixture within the residence time chamber. The sample is then directed to a sampling train which is configured to remove a desired material from the sample for subsequent analysis.

The invention may be embodied in other forms without departing from the spirit or novel characteristics thereof. The embodiments disclosed in this application are to be considered in all respects as illustrative and not limitative. The scope of the invention is indicated by the appended claims rather than by the foregoing description; and all changes which come within the meaning and range of equivalency of the claims are intended to be embraced therein.

The invention claimed is:

1. A method of sampling emission products from an emissions source, comprising:
   directing a sample of a gas stream from the emissions source into a dilution apparatus;
   in the dilution apparatus, cooling the gas stream sample with a dilution gas and thereafter introducing the dilution gas into the gas stream sample to mix with the gas stream sample;
   directing the gas mixture to a residence time chamber; and
   taking a sample of the gas mixture from the residence time chamber through a sampling probe having an inlet substantially parallel to a direction of flow of the gas mixture within the residence time chamber.

2. The method of claim 1, wherein the gas stream sample is cooled to substantially ambient temperature.

3. The method of claim 1, comprising introducing the dilution gas into the gas stream sample in a direction substantially perpendicular to a direction of flow of the gas stream sample in the dilution apparatus.

4. The method of claim 1, comprising taking samples of the gas mixture from the residence time chamber through a plurality of sampling probes each having an inlet substantially parallel to a direction of flow of the gas mixture within the residence time chamber.

5. The method of claim 4, comprising simultaneously collecting particulate matter, inorganic gas-phase, and volatile and semi-volatile organic matter samples.

6. The method of claim 1, wherein the residence time chamber has a longitudinal axis which is substantially perpendicular to the longitudinal axis of the dilution apparatus.

7. The method of claim 1, comprising changing the dilution ratio of the gas stream sample and the dilution gas.

8. A method of sampling emission products from an emissions source, comprising:
   directing a sample of a gas stream from the emissions source into a mixing chamber of a dilution apparatus;
   in the dilution apparatus, cooling the gas stream sample in the mixing chamber as a result of indirect heat exchange with a dilution gas and thereafter introducing the dilution gas into the mixing chamber;
   directing a mixture of the gas stream sample and the dilution gas to a residence time chamber; and
   taking a sample of the mixture from the residence time chamber through a sampling probe having an inlet substantially parallel to a direction of flow of the mixture within the residence time chamber.

9. The method of claim 8, wherein the gas stream sample is cooled to substantially ambient temperature.

10. The method of claim 8, comprising introducing the dilution gas into the mixing chamber in a direction substantially perpendicular to a direction of flow of the gas stream sample in the mixing chamber.

11. The method of claim 8, comprising taking samples of the mixture from the residence time chamber through a plurality of sampling probes each having an inlet substantially parallel to a direction of flow of the mixture within the residence time chamber.

12. The method of claim 11, comprising simultaneously collecting particulate matter, inorganic gas-phase, and volatile and semi-volatile organic matter samples.

13. The method of claim 8, comprising changing the dilution ratio of the gas stream sample and the dilution gas.

14. The method of claim 8, wherein the residence time chamber has a longitudinal axis which is substantially perpendicular to the longitudinal axis of the dilution apparatus.

* * * * *